(12) United States Patent (10) Patent No.: US 12,678,254 B2
Lum (45) Date of Patent: Jul. 14, 2026

(54) DRAPE MANAGEMENT SYSTEM

(71) Applicant: Cilag GmbH International, Zug (CH)

(72) Inventor: Richard Mark Lum, San Jose, CA (US)

(73) Assignee: Cilag GmbH International, Zug (CH)

( * ) Notice: Subject to any disclaimer, the term of this patent is extended or adjusted under 35 U.S.C. 154(b) by 234 days.

(21) Appl. No.: 18/670,850

(22) Filed: May 22, 2024

(65) Prior Publication Data

US 2024/0415596 A1     Dec. 19, 2024

Related U.S. Application Data

(60) Provisional application No. 63/508,116, filed on Jun. 14, 2023.

(51) Int. Cl.
    A61B 46/10        (2016.01)
    A61B 34/30        (2016.01)

(52) U.S. Cl.
    CPC .............. A61B 46/10 (2016.02); A61B 34/30 (2016.02)

(58) Field of Classification Search
    None
    See application file for complete search history.

(56) References Cited

U.S. PATENT DOCUMENTS

2017/0290632 A1* 10/2017 Nakatsu ................. A61B 34/30
2019/0046284 A1*  2/2019 Pennoyer .............. A61B 34/35
2019/0099232 A1*  4/2019 Soto ...................... A61B 46/10
2020/0390511 A1* 12/2020 Pennoyer, IV ......... A61B 46/10
2021/0393361 A1* 12/2021 Keim ..................... A61B 90/98

* cited by examiner

*Primary Examiner* — Michael W Kahelin
(74) *Attorney, Agent, or Firm* — FBT Gibbons LLP

(57)         ABSTRACT

Sterile drapes for surgical robotic systems include an excess of drape material to allow movement of components of the system. This excess of drape material is managed by one or more flat coiled springs attached to a surface of a sheath shape that forms the drape, near the closed end of the sheath shape. The coiled springs have a curvature on a flat side that is oriented toward the hollow interior of the sheath shape, and may be attached to the exterior surface of the sheath along the length of the springs in a flat, extended position. The coiled springs are configured to retract the closed end of the sheath toward the hollow interior as the robotic system moves to a position exposing an excess of drape material; and to release an excess of drape material as required to allow the opposite movement of the robotic system.

20 Claims, 6 Drawing Sheets

HEAD

LEGS

HEAD

LEFT

RIGHT

LEGS

DRAPE MANAGEMENT SYSTEM

PRIORITY

This application claims priority to U.S. Provisional Pat. App. No. 63/508,116, entitled "Drape Management System," filed Jun. 14, 2023, the disclosure of which is incorporated by reference herein, in its entirety.

TECHNICAL FIELD

The systems and methods disclosed herein are directed to devices and methods for utilizing sterile drapes with surgical robotic systems, and more particularly to managing excess drape material when a portion of a surgical robotic system moves while covered by a sterile drape.

BACKGROUND

A robotically enabled medical system is capable of performing a variety of medical procedures, including both minimally invasive procedures, such as laparoscopy, and non-invasive procedures, such as endoscopy (e.g., bronchoscopy, ureteroscopy, gastroscopy, etc.).

Such robotic medical systems may include robotic arms configured to control the movement of surgical tools during a given medical procedure. In order to achieve a desired pose of a surgical tool, a portion of a robotic arm may move with respect to other portions of the arm in order to position the surgical tool.

During surgical procedures, a sterile drape may be positioned to cover portions of the robotic systems, such as the robotic arms. The sterile drape is typically a disposable sheeting material that protects the sterile environment. In general, the sterile drape creates a boundary between the draped portion(s) of the robotic system and the sterile environment. For example, one or more sterile sheets may wrap around portions of the robotic system to create the boundary.

A draped robotic system component may move during a medical procedure. For example, an endoscopic tool may be moved back and forth to advance and retract a tool during a surgical procedure. The surgical drape should continue to function without hindrance during such movement of the robotic system.

SUMMARY

Excess drape material may be fitted over robotic system components to facilitate the movement of such components without stretching or damaging the drape material. When a robotic system component is in a first position (e.g., the component is extended), the drape material covering that component may closely fit the component. However, when the robotic system component is in a second position (e.g., the component is retracted), an excess of the drape material may hang off of the robotic system component. This excess drape material may obscure the view of the surgical site, interfere with changing the surgical tool, interfere with movement of the robotic system, or interfere with access to the patient.

Accordingly, a system to manage drape material is desirable. In particular, there is a need for a system that facilitates fitting an excess of drape material so as to safely cover moving parts of the robotic system, while at the same time minimizing the risk that this excess of material droops or hangs off the robotic system causing potential problems.

As disclosed herein, a drape management system automatically retracts an excess portion of the drape material when a draped portion of the robotic system moves while in operation. The drape management system also expands or extends the excess of drape material when the draped portion of the robotic system moves in the opposite direction to require use of the excess drape material. The management system may use one or more coiled springs attached to a portion of the drape material that would otherwise tend to droop or hang off the robotic system when the draped portion of the robotic system moves while in operation.

A coiled spring is biased to coil up in a relaxed position and is biased to maintain this coiled shape. One or more of the coiled springs is extended flat and attached uncoiled to a portion of the drape material that will become an excess of drape material when the robotic system or components of the system move during operation while covered with a drape, such that the system under the drape may become larger, smaller, shorter, or longer. The coiled spring is thus biased to retract the excess portion of the drape material when the draped component of the robotic system moves to expose the excess portion of the drape material. The coiled spring also allows the excess of drape material to gradually extend as needed when movement of the robotic system pulls on the excess drape material or otherwise uncoils the coiled spring. In this manner, the drape material may fit closely over the draped portion of the robotic system without excess drape material hanging off or drooping, even when the draped portion of the robotic system moves while in operation. Accordingly, the disclosed system and/or method have several advantages. For example, the disclosed system and/or method advantageously avoid obscuring the view of the surgical site, interfering with changing the surgical tool, interfering with movement of the robotic system, or interfering with access to the patient. Further, the disclosed system and/or method manage excess drape material simply and automatically, with little or no human intervention, and without manually tying, taping or strapping, or bundling the excess drape material.

The systems, methods, and devices of this disclosure each have several innovative aspects, no single one of which is solely responsible for the desirable attributes disclosed herein.

In accordance with some embodiments, the drape management system includes an elongated surgical drape in the shape of a sheath configured to cover at least a portion of a surgical robotic system. The system includes a coiled spring attached to the sheath near the closed end. The spring has a coiled resting position and a flat extended position, so that in the coiled resting position, the spring is configured to retract the end of the sheath along its length, and when the spring is extended, the sheath is able to extend in length.

In some embodiments, the sheath includes a hollow interior so as to cover at least a portion of an arm of the surgical robotic system. The coiled spring has a direction of curvature that is oriented toward the hollow interior so as to bias the spring to retract the end of the sheath. The coiled spring may be a coiled flat strip with two flat sides, and attached to the sheath in a direction parallel to the length of the sheath.

In some embodiments, the direction of curvature is along the flat side of the coiled spring that is attached to the sheath. The coiled spring may be a plastic material, such as a polycarbonate resin thermoplastic, and may be removably attached to a surface of the sheath, such as with adhesive tape.

Embodiments may also utilize a second coiled spring attached parallel to and nearby the first coiled spring and near the end of the drape. The second coiled spring may likewise be a coiled, flat strip with two flat sides, and have a coiled resting position and a flat extended position. In the coiled resting position, the second coiled spring may be configured to retract the end of the sheath along the length of the sheath, and when in the extended position, the second coiled spring may be configured to extend the end of the sheath along the length of the sheath.

In accordance with some embodiments, the second coiled spring in the coiled resting position may include a direction of curvature that is oriented toward the hollow interior of the drape. The direction of curvature of the second spring biases the second spring to retract the end of the sheath.

In some embodiments, the first coiled spring and the second coiled spring may be parallel to each other when in the extended position, and parallel to the length of the sheath. Both coiled springs may be attached to an exterior of the sheath along their lengths.

Exemplary embodiments may configure the flexible sheath forming the drape to cover a tool stage with a moveable tool carriage positioned thereon, wherein the sheath has a length and a closed end and is configured to attach to the tool carriage between the ends of the sheath. Two coiled springs may be attached to the sheath with direction of curvature oriented toward the hollow interior of the sheath, such that the coiled springs are configured to retract the end of the sheath along the length of the sheath.

In some embodiments, responsive to relative movement between the carriage and the stage, the coiled spring is configured to move between the coiled resting position, in which the sheath is in the retracted position, and the flat extended position, in which the sheath is extended along the length of the sheath.

The drape management may also include embodiments in which the coiled spring is attached to the sheath at a position between the end of the sheath and the attachment of the sheath to the tool carriage. In some embodiments, two coiled springs may be attached to the sheath near the end, wherein the second spring has a coiled resting position and a flat extended position. The second spring may be attached to the sheath in the flat extended position parallel to the first spring, with the coiled resting position of the second spring having a direction of curvature oriented toward the hollow interior of the sheath. When in the coiled resting position, the second spring is configured to retract the end of the sheath along the length of the sheath.

The various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the detailed description has been principally selected for readability and instructional purposes and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive procedures, such as laparoscopy, and non-invasive procedures, such as endoscopy. Among endoscopy procedures, such a system may be capable of performing bronchoscopy, ureteroscopy, gastroscopy, etc.

In addition to performing a breadth of procedures, such a system may provide additional benefits, such as enhanced imaging and guidance to assist the physician. Additionally, such a system may provide the physician with the ability to perform procedures from an ergonomic position, without the need for awkward arm motions and positions. Still further, such a system may provide the physician with the ability to perform procedures with improved ease of use such that one or more of the instruments of the system can be controlled by a single user.

During surgical procedures, a sterile drape may be positioned to cover one or more portions of the robotic system, such as covering the robotic arms. The sterile drape serves to protect the sterile environment. Such a sterile drape creates a boundary between the draped portion(s) of the robotic system and the surgical site.

Various embodiments are described below in conjunction with the drawings for purposes of illustration. Many other embodiments of the disclosed concepts are possible, and various advantages can be achieved with the disclosed embodiments. Headings are included herein for reference and to aid in locating various sections. These headings are not intended to limit the scope of the concepts described with respect thereto. Such concepts may have applicability throughout the entire specification.

2. Robotic System

Figure 1A:
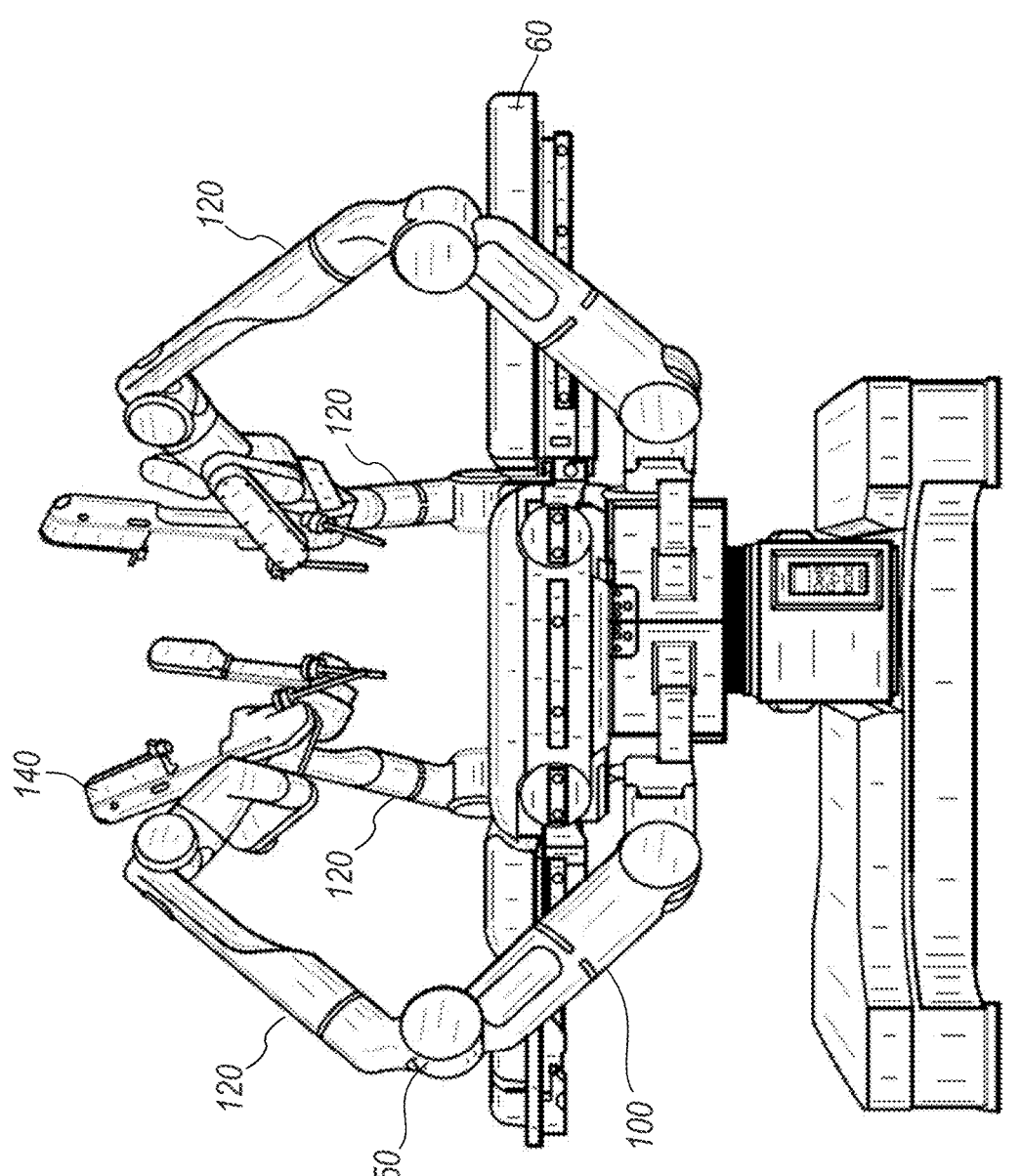
FIG. 1A illustrates an example robotic medical system in which the drape management system described herein may be implemented.

FIG. 1A illustrates an exemplary robotic medical system 100 according to some embodiments. In some embodiments, the robotic medical system 100 is a robotic surgery system. In the example of FIG. 1A, the robotic medical system 100 comprises a patient support platform 60 (e.g., a patient platform, a table, a bed, etc.). One end of the patient support platform 60 is referred to as the "head" and the other end as the "leg."

The robotic medical system 100 includes one or more robotic arms 120. In some embodiments, the robotic arms 120 can be configured to perform robotic medical procedures. Although FIG. 1A shows four robotic arms 120, the robotic medical system 100 may include any number of robotic arms, including more or fewer than four.

A robotic arm 120 can be positioned relative to the patient support platform 60 by translating the robotic arm 120 and/or by adjusting a position and/or orientation of the robotic arm 120 via one or more joints 150 and/or links.

Figure 1B:
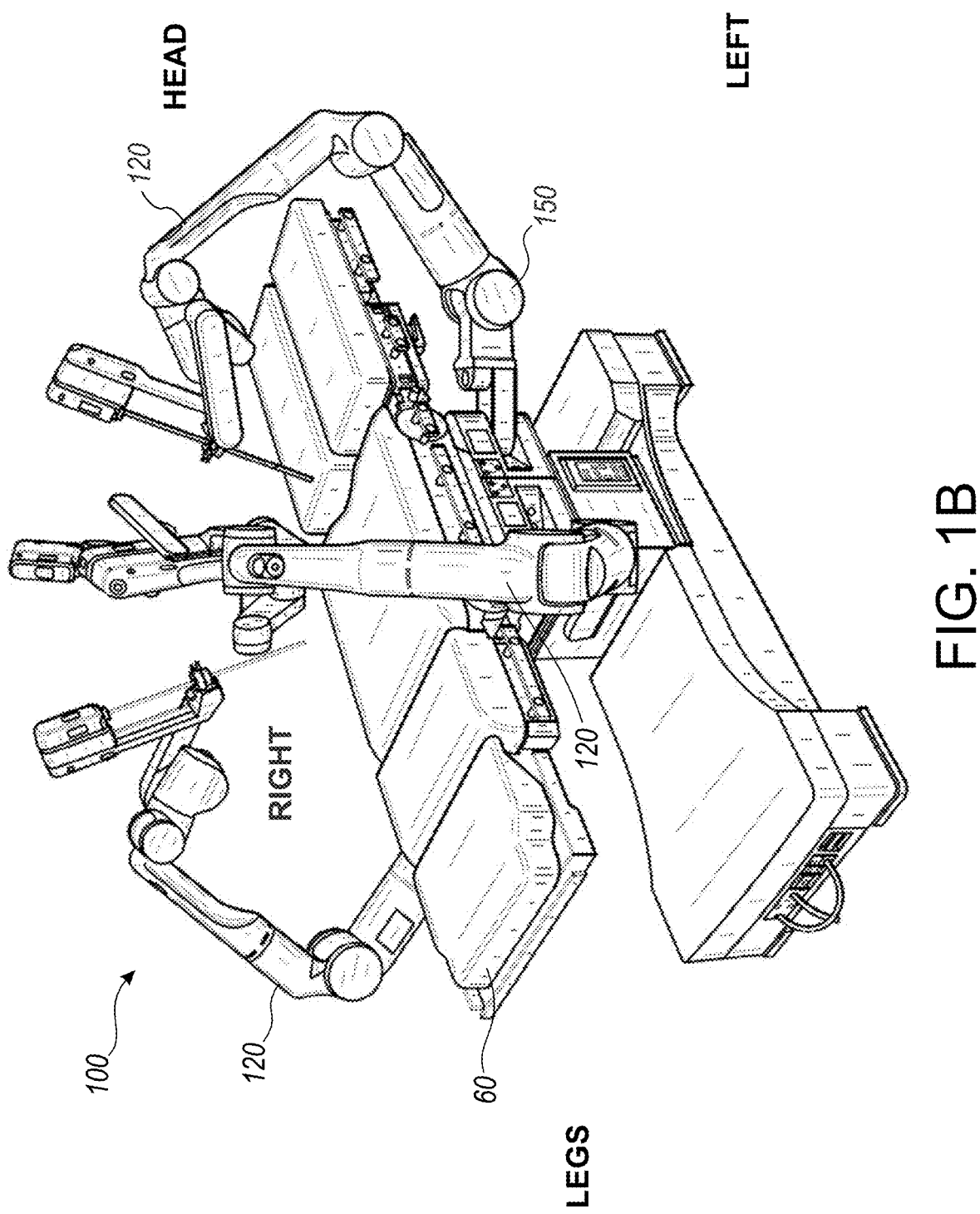
FIG. 1B is a perspective view of an example robotic medical system in which the drape management system described herein may be implemented.
Figure 1C:
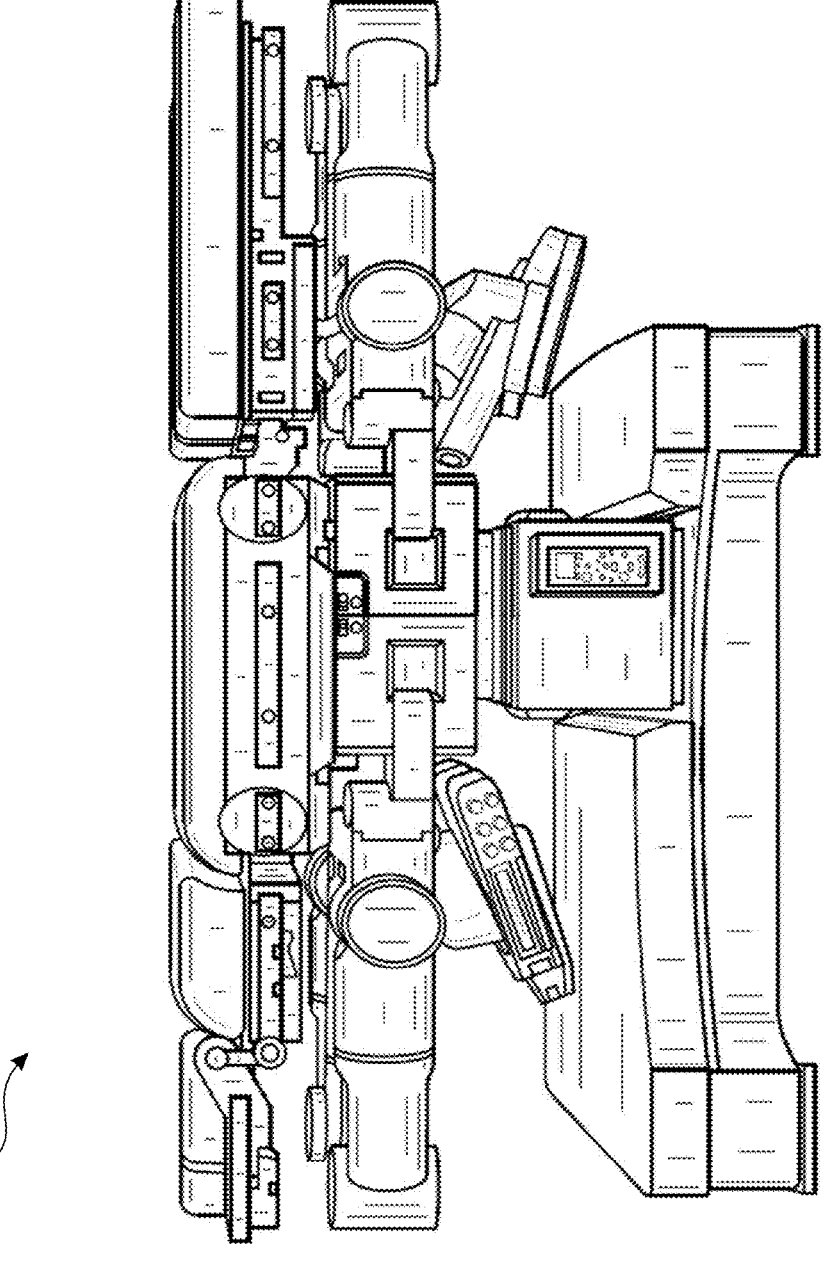
FIG. 1C depicts an example robotic medical system in a non-operational state and in which the drape management system described herein may be implemented.
Figure 2A:
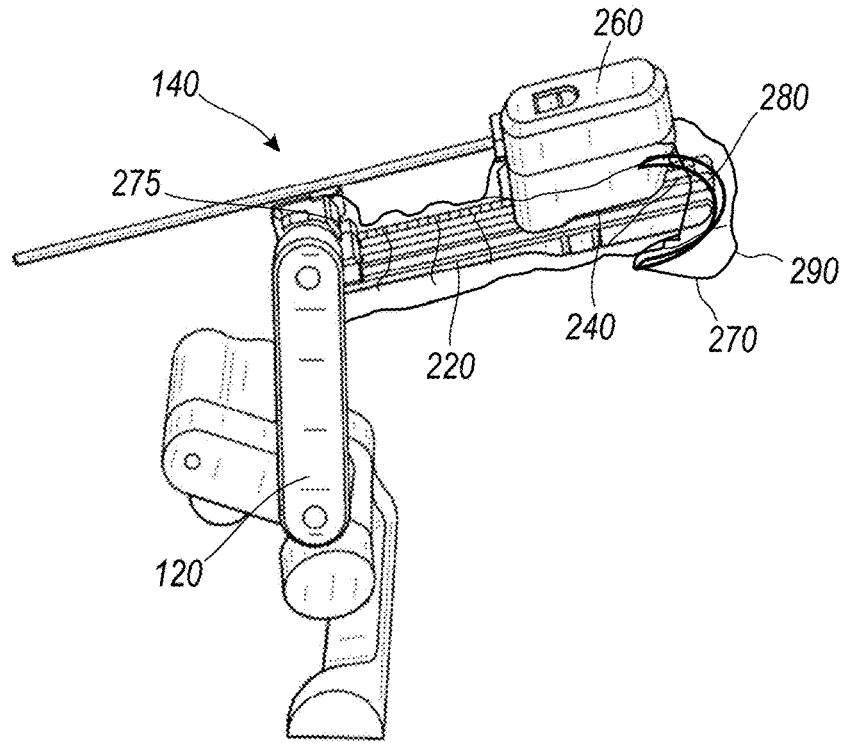
FIGS. 2A and 2B illustrate a drape management system in accordance with some embodiments, with the robotic system shown in two positions, one position with an excess portion of drape material retracted and another position with the drape material extended.
Figure 2B:
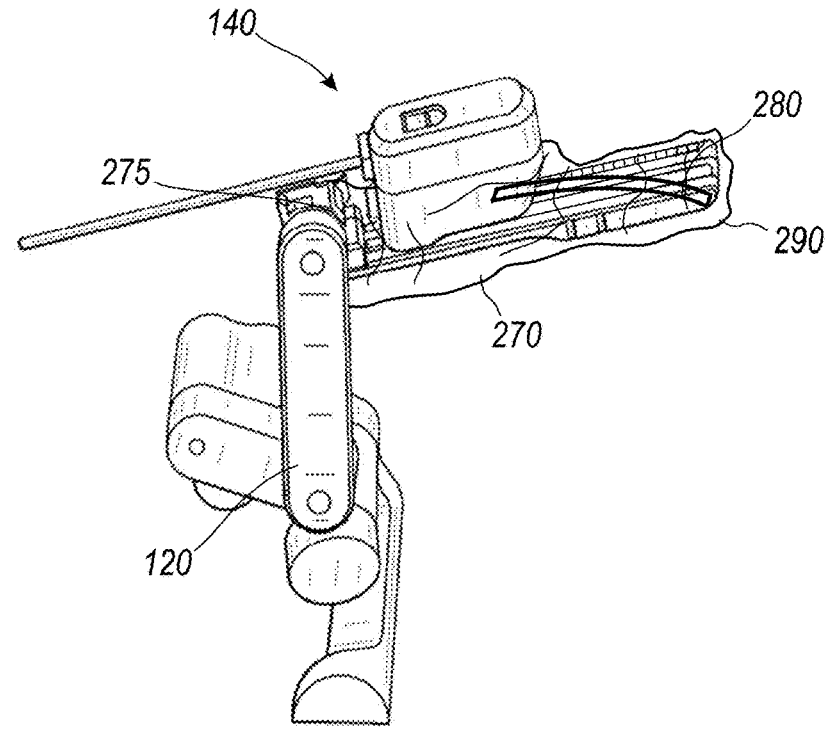

During a robotic medical procedure, one or more of the robotic arms 120 can include a tool drive 140 positioned on a distal end of the robotic arm 120 and configured to hold tools, such as a tool 260 shown in FIGS. 2A, 2B (e.g., robotically controlled medical instruments, such as an endoscope and/or any other instruments (e.g., sensors, illumination instrument, cutting instrument, etc.) that may be used during surgery), and/or be coupled to one or more accessories, including one or more cannulas, in accordance with some embodiments. FIG. 1B is a perspective view of the robotic medical system 100, in accordance with various embodiments. FIG. 1C depicts the example robotic medical system 100 in a non-operational state, with the robotic arms 120 stowed under the patient support platform 60 because the robotic arms 120 are not in use.

FIGS. 2A and 2B illustrate a tool drive 140 mounted at the distal end of a robotic arm 120, in accordance with various embodiments. The tool drive 140 may be configured to couple to various surgical tools, such as tool 260 (e.g., an endoscope). Tool 260 is mounted on a tool carriage 240, which is translatable on a stage 220 by electric motors. In operation, the carriage 240 is translated proximally (e.g., proximal relative to the robotic arm 120) along the stage 220 toward a surgical site, as shown in FIG. 2B. The carriage 240 may also be translated distally (e.g., distal relative to the robotic arm 120) along the stage 220 away from the surgical site, as shown in FIG. 2A. Such translations of the carriage 240 (and the tool 260 mounted on the carriage 240) along the stage 220 may occur many times during a surgical procedure, and may occur in connection with other movements of the robotic arm 120.

3. Drape Management

In some embodiments, the tool drive 140, including the stage 220 and carriage 240, are covered by a sterile drape 270. For example, drape 270 may comprise a sterile polyurethane sheath that is placed over and wraps around the stage 220 and carriage 240. The drape 270 may have the general shape of a sheath with an open end 275 and a closed end 290, which may facilitate placing the drape 270 over the stage 220 and carriage 240. However, in some embodiments, the open end 275 may mate with another sheath covering additional components (e.g., the robotic arm 120) such that the open end 275 is thereby closed. In some embodiments, the open end 275 may couple to a component of the robotic medical system 100 such that the open end 275 is closed or sealed by that component. In some embodiments, the drape 270 may cover additional components of the robotic medical system 100, such as the robotic arm 120. In some embodiments, the closed end 290 may be partially or fully open. The tool 260 may connect on top of the carriage 240 and include electrical or mechanical connections (not shown) extending through the drape 270 (e.g. through appropriately sized and shaped orifices in the drape 270).

As illustrated in FIGS. 2A and 2B, the drape 270 covers the stage 220 and carriage 240 while the carriage 240 translates back and forth along the stage 220. If the length of drape 270 were the same as the length of the stage 220, then as the carriage 240 moves proximally as shown in FIG. 2B, the drape 270 may stretch or tear due to relative movement between the carriage 240 and stage 220. Instead, as illustrated in FIGS. 2A and 2B, the drape 270 includes an excess length of drape material, or "slack," in order to accommodate this movement of the carriage 240.

As illustrated in FIG. 2A, when the carriage 240 and tool 260 are translated to a distal position on the stage 220, an excess of drape material is located near closed end 290. In FIG. 2A, this excess of drape material is unused and, unless managed, would tend to hang off of or droop from the stage 220, and potentially obscure the view of the surgical site or interfere with movement of other parts of the robotic medical system 100. Accordingly, a coiled spring 280 may be used to automatically retract the closed end 290 of drape 270 as the carriage 240 is translated to a distal position. The coiled spring 280 may be attached to the drape 270 along the length of coiled spring 280, while drape 270 is flat and the coiled spring 280 is in an extended position, as discussed in more detail below. Thus, the bias of coiled spring 280 to return to its coiled position may retract any excess of drape material near the closed end 290 of drape 270.

As illustrated in FIG. 2B, when the carriage 240 is translated to a proximal position on the stage 220, such as to move the tool 260 closer to the surgical site, the excess of drape material described above is gradually taken up as needed to cover the increasing distance from the carriage 240 to the end of the stage 220 adjacent to the closed end 290 of the drape 270. As the excess of drape material is taken up, the spring 280 is gradually extended from its coiled resting position until it is flat or nearly flat when the carriage 240 is fully translated to its most proximal position. In this manner, normal movement of the robotic medical system 100 is unlikely to excessively stretch or tear the drape 270 and avoids compromising the sterile environment.

Figure 3A:
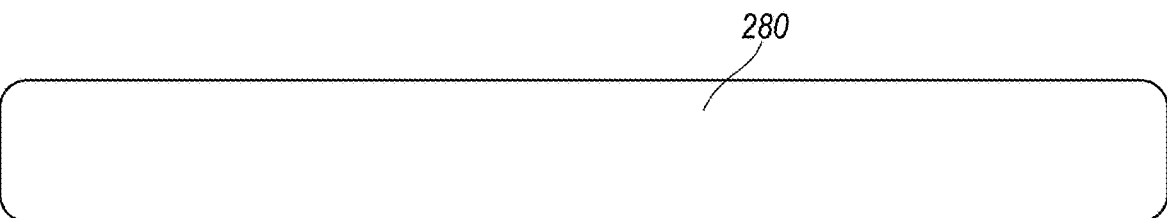
FIGS. 3A-3C illustrate different views of a coiled spring that is used with an exemplary drape management system according to some embodiments.
Figures 3B, 3C:
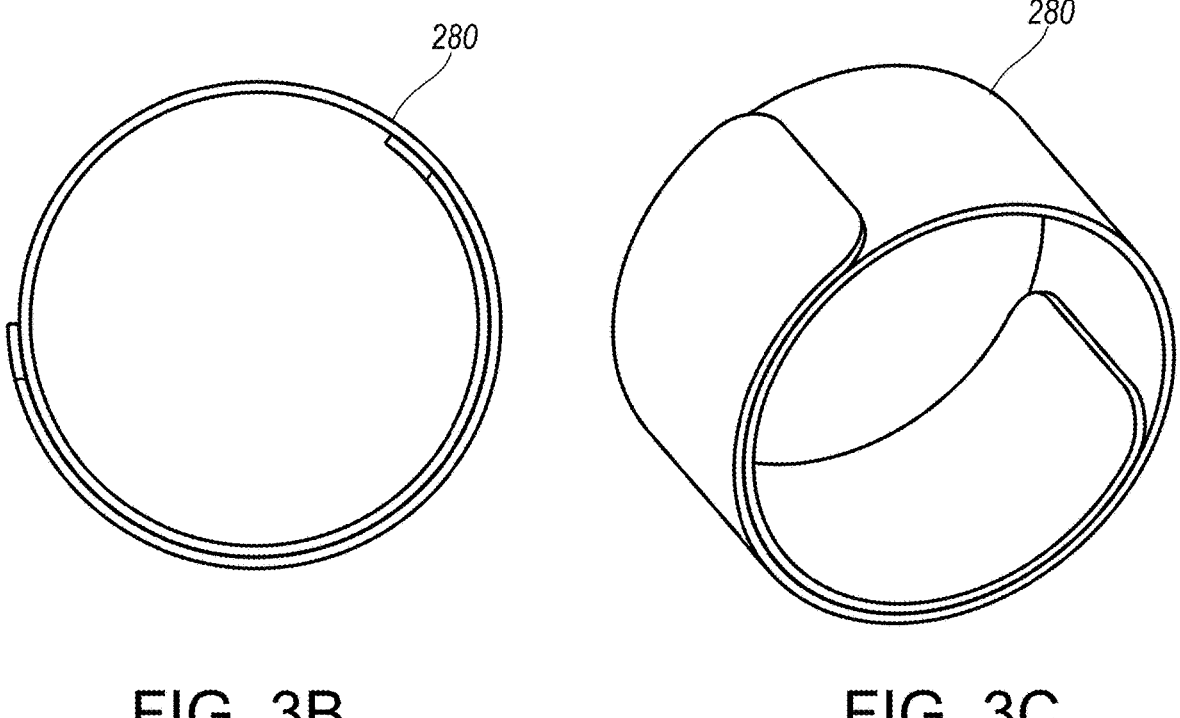

FIGS. 3A-3C illustrate the spring 280, in accordance with various embodiments. The top plan view of FIG. 3A shows the spring 280 in a fully extended, flat position. The spring 280 may comprise an elongated, thin, and flat strip, with two substantially flat sides. In FIGS. 3B and 3C, the spring 280 is shown in a coiled resting state. The spring 280 is biased to return to this coiled resting state.

Spring 280 may comprise spring materials, such as metal alloys. Alternatively, spring 280 may comprise a plastic material, such as a polycarbonate resin thermoplastic. Optically transparent thermoplastics, such as Lexan® by SABIC Global Technologies B.V., or equivalent transparent thermoplastics, may be used so that when the coiled spring 280 is extended flat and attached to the drape 270, the spring 280 does not obscure the view of any underlying parts of the robotic medical system 100, or potentially obscure portions of the surgical site.

Figure 4A:
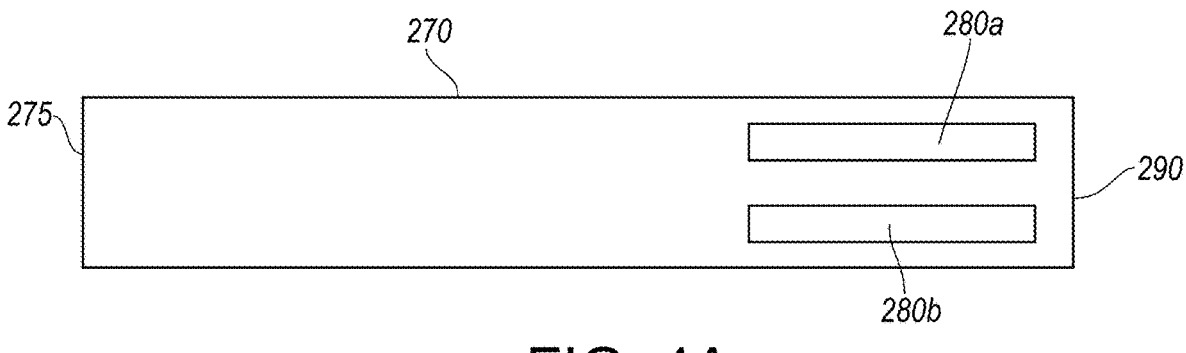
FIGS. 4A and 4B are a plan view and enlarged plan view, respectively, illustrating a drape with two attached coiled springs as used with an exemplary drape management system according to some embodiments.
Figure 4B:
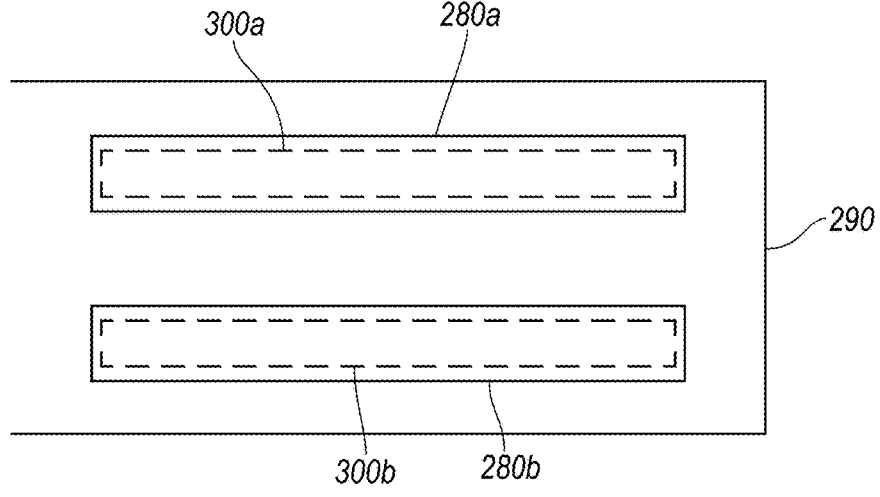

An embodiment of the drape management system is illustrated in FIGS. 4A and 4B. There, drape 270, which may have the general shape of a sheath, being open at one end and closed at the opposite end, is shown laid flat in a top view. The sheath shape of drape 270 forms a hollow interior and is sized to cover a desired portion of the robotic medical system 100, terminating in the closed end 290. By way of example, the drape 270 may be formed from a sterile, flexible polyurethane sheeting material. In this manner, drape 270 may also be optically translucent or transparent so that personnel may observe parts of the robotic medical system 100 within the hollow interior of the sheath shape forming drape 270.

To facilitate retraction and extension of excess drape material near the closed end 290, two coiled springs 280a and 280b may be positioned near the closed end 290. By "near" the closed end 290, it is meant that the coiled springs 280a and 280b may be positioned anywhere from immediately abutting the closed end 290 to a few inches behind the closed end 290 (i.e., the distance between the closed end 290 and the closest end of the respective spring 280a or 280b is less than one third of the length of the drape 270). When the tool 260 is connected on top of the carriage 240 with electrical or mechanical connections extending through the drape 270 (see FIGS. 2A and 2B), the coiled springs 280a and 280b should extend forward of any such connection and toward the closed end 290 of the drape 270.

To facilitate translation of the carriage 240 on the stage 220 without harming the drape 270, the excess length of drape material needed for the embodiment of FIGS. 2A and 2B may be approximately the same length as the distance of translation of the carriage 240 in one direction. To facilitate the retraction of a substantial portion of this excess drape material, the coiled springs 280a and 280b may have an extended length similar to the length of the excess drape material that is used to accommodate expected movement of the robotic medical system 100.

As illustrated in FIGS. 4A and 4B, when attached to drape 270, coiled springs 280a and 280b may be extended in a flat position and aligned parallel to each other and parallel to the length of the sheath shape of the drape 270. FIG. 4B is an enlarged view of the end of FIG. 4A where springs 280a and 280b attach to the drape 270. Springs 280a and 280b may be attached to the interior or exterior surface of the sheath shape of the drape 270. Advantageously, when springs 280a and 280b are attached to the exterior surface of the sheath shape of the drape 270, springs 280a and 280b may be attached without turning the sheath shape of the drape 270 inside out, which may be difficult if the drape 270 has restrictions such as ports (not shown) used to make electrical connections across the drape 270. Attaching the springs 280a and 280b on the exterior of the sheath shape of the drape 270 also has the advantage that movement of parts of the robotic medical system 100 beneath the drape 270 is less likely to dislodge or tear off the springs 280a and 280b.

As illustrated in FIGS. 3B and 3C, the spring 280 has a direction of curvature which forms the coiled shape. As illustrated in FIGS. 4A and 4B, each of the coiled springs 280a and 280b may be attached to the exterior of the sheath shape of the drape 270. Orienting this direction of curvature of each spring 280a and 280b downward and toward the hollow interior of the drape 270 facilitates retraction of the excess drape material into the area of the hollow interior of the drape 270. In this manner, the sheath shape may desirably collapse into itself lengthwise, as opposed to being retracted outwardly and potentially interfering with movement of the robotic medical system 100.

Springs 280a and 280b may be attached to drape 270 by any suitable technique for mechanical attachment, such as heat welding, gluing, riveting, or taping. In some embodiments, springs 280a and 280b may be attached with adhesive to the drape 270. For example, a double-sided adhesive may be used in the area 300a and 300b between springs 280a and 280b and the exterior of drape 270. In some embodiments, one side of the adhesive may be attached to the drape or the springs 280a and 280b, and the other side of the adhesive left with the release liner in place. When ready for use, the release liner may be removed and the other side of the double-sided tape may be adhered to the other of the drape 270 or coiled springs 280a and 280b. An example of a double-sided tape is 3M™ Double-Coated Transparent Polyethylene Medical Tape 9889, by 3M Company. In this manner, the coiled springs 280a and 280b may be stored separately from the drape 270, thus conserving space, and the coiled springs 280a and 280b may be adhered to the drape 270 prior to use. In addition, using an adhesive to attach the coiled springs 280a and 280b may permit removing and/or reattaching the coiled springs 280a and 280b when necessary for storage, disposal, recycling, etc. In some embodiments, the coiled springs 280a and 280b may be inserted within hollow portions on the drape 270 that are dedicated to housing the coiled springs 280a and 280b and are separate from other hollow portion(s) of the drape 270. In some embodiments, a single coiled spring 280 is used, and in other embodiments, two or more coiled springs 280 are used. In the various embodiments described above, the coiled springs 280a and 280b may be detachable or otherwise removable from the drape 270.

As used herein, the term "exemplary" means "serving as an example, instance, or illustration," and does not necessarily indicate any preference or superiority of the example over any other configurations or implementations.

As used herein, the term "and/or" encompasses any combination of listed elements. For example, "A, B, and/or C" includes the following sets of elements: A only, B only, C only, A and B without C, A and C without B, B and C without A, and a combination of all three elements, A, B, and C.

The term "approximately" and similar terms denote a range that is within 10% of the stated value.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. For example, it will be appreciated that one of ordinary skill in the art will be able to employ a number of corresponding alternative and equivalent structural details, such as equivalent ways of fastening, mounting, coupling, or engaging components and equivalent mechanisms for producing particular actuation motions. Thus, the present invention is not intended to be limited to the embodiments shown herein but is to be accorded the widest scope consistent with the principles and novel features disclosed herein.

What is claimed is:

1. A surgical drape comprising:
an elongated, flexible sheath configured to cover at least a portion of a surgical robotic system, wherein the sheath has a length and an end; and
a first spring attached to the sheath near the end, wherein the first spring has a coiled resting position and a flat extended position,
wherein, when in the coiled resting position, the first spring is configured to retract the end of the sheath along the length, and when in the extended position, the first spring is configured to extend the end of the sheath along the length.

2. The surgical drape of claim 1, wherein:
the sheath further includes a hollow interior configured to cover at least a portion of an arm of the surgical robotic system; and
the first spring in the coiled resting position includes a direction of curvature oriented toward the hollow interior, wherein the direction of curvature is configured to bias the first spring to retract the end of the sheath.

3. The surgical drape of claim 2, wherein, when in the coiled resting position, the first spring is a coiled flat strip with two flat sides.

4. The surgical drape of claim 3, wherein one flat side of the first spring is attached to the sheath in a direction parallel to the length of the sheath.

5. The surgical drape of claim 4, wherein the flat side of the first spring attached to the sheath forms the direction of curvature.

6. The surgical drape of claim 1, wherein the first spring is removably attached to an interior surface of the sheath.

7. The surgical drape of claim 1, wherein the first spring is removably attached to an exterior surface of the sheath.

8. The surgical drape of claim 1, wherein the first spring is a plastic material.

9. The surgical drape of claim 8 wherein the first spring is a polycarbonate resin thermoplastic.

10. The surgical drape of claim 1, wherein the first spring is adhesively attached to the sheath.

11. The surgical drape of claim 5, comprising:

a second spring attached to the sheath near the end, wherein the second spring has a coiled resting position and a flat extended position, and when in the coiled resting position, the second spring is a coiled, flat strip with two flat sides; and wherein, when in the coiled resting position, the second spring is configured to retract the end of the sheath along the length, and when in the extended position, the second spring is configured to extend the end of the sheath along the length.

12. The surgical drape of claim 11, wherein:

the second spring in the coiled resting position includes a direction of curvature oriented toward the hollow interior; and the direction of the curvature of the second spring is configured to bias the second spring to retract the end of the sheath.

13. The surgical drape of claim 12, wherein the first spring and the second spring are parallel to each other when in the extended position.

14. The surgical drape of claim 12, wherein:

the first spring and the second spring both have a length when the first spring and the second spring are in the extended position;

the first spring is attached to the sheath along the length of the first spring; and the second spring is attached to the sheath along the length of the second spring.

15. The surgical drape of claim 12, wherein the first spring and the second spring are both attached to the sheath on an interior surface thereof.

16. The surgical drape of claim 12, wherein the first spring and the second spring are both attached to the sheath on an exterior surface thereof.

17. A surgical drape comprising:

an elongated, flexible sheath configured to cover a tool stage with a moveable tool carriage positioned thereon, wherein the sheath has a length and an end and is configured to attach to the tool carriage at a position before the end of the sheath; and a first spring attached to the sheath near the end, wherein the first spring has a coiled resting position and a flat extended position, wherein, when in the coiled resting position, the first spring has a direction of curvature oriented toward a hollow interior of the sheath and is configured to retract the end of the sheath along the length.

18. The surgical drape of claim 17, wherein the first spring is attached to the sheath in a direction parallel to the length of the sheath.

19. The surgical drape of claim 18, wherein, responsive to relative movement between the carriage and the tool stage, the first spring is configured to move between the coiled resting position, in which the sheath is in the retracted position, and the flat extended position, in which the sheath is extended along the length of the sheath.

20. The surgical drape of claim 19, wherein the first spring is attached to the sheath at a position between the end of the sheath and the attachment of the sheath to the tool carriage.

* * * * *